US 6,623,420 B2

(12) United States Patent
Reich et al.

(10) Patent No.: US 6,623,420 B2
(45) Date of Patent: Sep. 23, 2003

(54) PHYSIOLOGICAL HEART PUMP CONTROL

(75) Inventors: Sanford Reich, Providence, RI (US); Edward Theodore Bullister, Weston, MA (US)

(73) Assignee: Apex Medical, Inc., East Walpole, MA (US)

( * ) Notice: Subject to any disclaimer, the term of this patent is extended or adjusted under 35 U.S.C. 154(b) by 0 days.

(21) Appl. No.: 10/219,872

(22) Filed: Aug. 15, 2002

(65) Prior Publication Data

US 2003/0045772 A1 Mar. 6, 2003

Related U.S. Application Data

(60) Provisional application No. 60/312,839, filed on Aug. 16, 2001.

(51) Int. Cl.$^7$ ................................................ A61M 1/10
(52) U.S. Cl. ........................................ 600/17; 623/3.28
(58) Field of Search .................. 600/16–17; 623/3.1, 623/3.28

(56) References Cited

U.S. PATENT DOCUMENTS

| | | | | |
|---|---|---|---|---|
| 4,310,930 A | * | 1/1982 | Goldowsky | 623/3.1 |
| 4,516,567 A | * | 5/1985 | Veragen | 600/16 |
| 5,352,180 A | * | 10/1994 | Candelon et al. | 600/17 |
| 5,385,581 A | * | 1/1995 | Bramm et al. | 623/3.14 |
| 5,888,242 A | | 3/1999 | Antaki et al. | |
| 6,048,363 A | * | 4/2000 | Nagyszalanczy et al. | 623/3.13 |
| 6,171,253 B1 | | 1/2001 | Bullister et al. | |
| 6,176,822 B1 | * | 1/2001 | Nix et al. | 600/17 |
| 6,264,601 B1 | * | 7/2001 | Jassawalla et al. | 600/16 |
| 6,310,930 B1 | * | 10/2001 | Peters et al. | 376/261 |
| 6,367,333 B1 | | 4/2002 | Bullister et al. | |

FOREIGN PATENT DOCUMENTS

WO    WO98/43688    * 10/1998    ............ A61M/1/10

OTHER PUBLICATIONS

Bullister et al, " A Blood Pressure Sensor for Long–Term Implantation," Artificial Organs, 2001, 25(5): 376–379.
Yuhki et al, " Detection of Suction and Regurgitation of the Implantable Centrifugal Pump Based on the Motor Current Waveform Analysis and its Application to Optimization of Pump Flow," 1999, Artificial Organs, 23(6):532–537.
Nakata et al, " A New Control Method That Estimates the Backflow in a Centrifugal Pump," 1999, Artificial Organs, 23(6):538–541.
Jarvik et al, " Belt Worn Control System and Battery for the Percutaneous Model of the Jarvik 2000 Heart," 1999, Artificial Organs, 23(6):487–489.
Waters et al, " Motor Feedback Physiological Control for a Continuous Flow Ventricular Assist Device, 1999," Artificial Organs, 23(6):480–486.
Giridharan et al, " Modeling and Control of Brushless DC Axial Flow Ventricular Assist Device," 2002, ASAIO Journal, pp: 272–289.

* cited by examiner

Primary Examiner—Kennedy Schaetzle
Assistant Examiner—Kristen Droesch
(74) Attorney, Agent, or Firm—Francis L. Conte (57) ABSTRACT

A blood pump is joined in parallel flow between the left ventricle and aorta of a patient's heart. The pump includes an inlet pressure sensor and cooperating controller for measuring inlet pressure to the pump to control operation thereof. The controller adjusts speed of the pump in a closed loop control using feedback of the measured inlet pressure to conform operation of the pump with the natural cycle of the heart.

33 Claims, 2 Drawing Sheets

PHYSIOLOGICAL HEART PUMP CONTROL

This application claims the benefit of U.S. Provisional Application No. 60/312,839; filed Aug. 16, 2001.

This invention was made with United States Government support under Cooperative Agreement No. 70NANB7H3059 awarded by NIST. The United States Government has certain rights in the invention.

BACKGROUND OF THE INVENTION

The present invention relates generally to heart assist pumps, and, more specifically, to control thereof in cooperation with the natural heart.

One form of heart dysfunction is the inability for the left ventricle to sufficiently pump blood over various levels of patient activity. Heart assist pumps have been undergoing development for many years for supplementing the pumping capability of the dysfunctional heart.

Since the heart is a muscle which pumps blood in periodic pulses in each heartbeat cycle, the heart assist pump must be capable of complementing natural heart flow without adversely affecting natural performance of the heart.

Many forms of heart assist pumps have undergone development, with different advantages and disadvantages. One form of heart assist pump made in small, implantable size is the Left Ventricular Assist Device (LVAD) which is sutured in flow communication between the left ventricle and the aorta. The LVAD operates in parallel flow with the left ventricle for collectively pumping the blood through the aorta for feeding the arterial branch.

The various heart assist pumps undergoing development have various sizes and configurations from large to small and from rotary to reciprocating. And, each of these pumps must be suitably controlled for pumping blood in conjunction with the left ventricle.

Recently, there have been significant advances in the development of heart assist pumps. Second and third generation rotary pumps are smaller and lighter and have demonstrated viability for long-term support. These pumps are being designed to be totally implantable and to enable patients to eventually leave the hospital and resume normal activities. These new generations of rotary pumps cannot rely on the simple passive fill mechanism that provided physiological control for the first generation of pulsatile heart pumps.

Since the left ventricle undergoes a diastolic filling cycle and systolic pumping cycle, the heart assist pump must be suitably controlled in conjunction with the pulsatile pumping of the natural heart.

Accordingly, it is desired to provide an improved heart assist pump and control system for supplementing blood pumping of the natural heart in situ.

BRIEF DESCRIPTION OF THE INVENTION

A blood pump is joined in parallel flow between the left ventricle and aorta of a patient's heart. The pump includes an inlet pressure sensor and cooperating controller for measuring inlet pressure to the pump to control operation thereof. The controller adjusts speed of the pump in a closed loop control using feedback of the measured inlet pressure to conform operation of the pump with the natural cycle of the heart.

BRIEF DESCRIPTION OF THE DRAWINGS

The invention, in accordance with preferred and exemplary embodiments, together with further objects and advantages thereof, is more particularly described in the following detailed description taken in conjunction with the accompanying drawings in which.

DETAILED DESCRIPTION OF THE INVENTION

Figure 1:
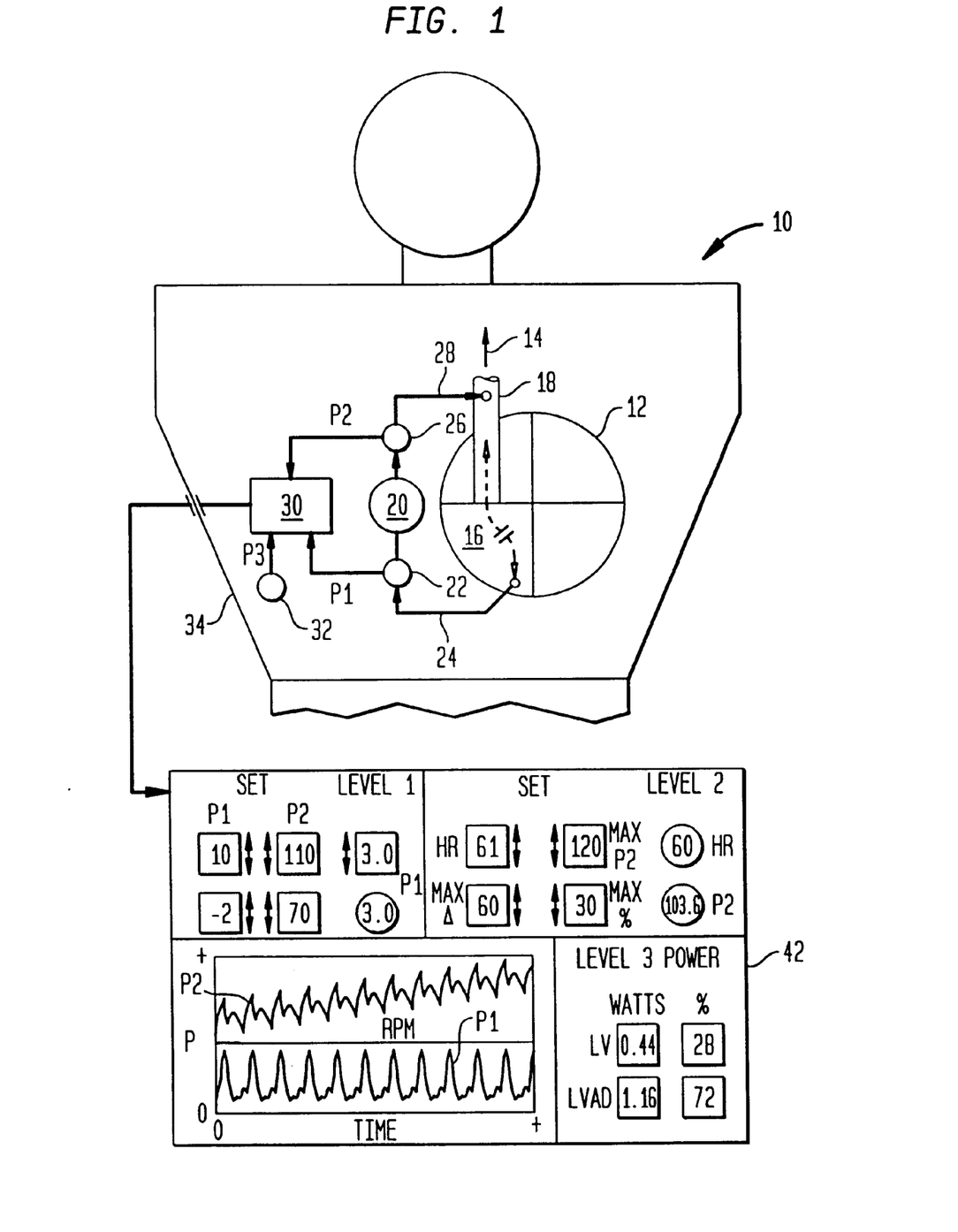
FIG. 1 is a schematic representation of an implanted blood pump and cooperating controller in accordance with an exemplary embodiment of the present invention, with an external monitor for initializing the controller and monitoring performance of operation.

Illustrated schematically in FIG. 1 is a living patient 10 having a dysfunctional heart 12 which lacks normal capability for pumping blood 14 through the arterial branch for all levels of activity from rest to strong exercise. In particular, the left ventricle 16 of the heart lacks capability to properly pump blood through the aorta 18 to feed the arterial system.

In accordance with the present invention, a blood pump 20 in the form of a Left Ventricular Assist Device (LVAD) is suitably implanted in the chest of the patient closely adjacent to the heart in flow communication between the left ventricle 16 and the aorta 18 for supplementing pumping capability of the left 19 ventricle.

The blood pump may have any conventional form, and in the preferred embodiment is a rotary or centrifugal pump having a suction inlet joined to the left ventricle and pressure outlet joined to the aorta. Performance of the rotary pump is conventionally rated by corresponding performance curves in which the flowrate through the pump corresponds with the differential pressure across the pump between the inlet and outlet thereof, and varies as the speed of the rotary impeller increases. Increasing impeller speed generally corresponds with increasing differential pressure and increasing flowrate through the pump.

As shown schematically in FIG. 1, the pump includes means in the form of an inlet pressure sensor 22 for measuring inlet pressure of the blood flow between the left ventricle and inlet side of the pump. The inlet pressure sensor may have any suitable form such as that disclosed in U.S. Pat. No. 6,171,253 and U.S. Pat. No. 6,367,333, both assigned to the present assignee, and both incorporated herein by reference. In these patents, a flat diaphragm is formed in a cannula through which the blood is channeled into the pump, and strain gauges are mounted on the diaphragm for measuring strain thereof which is indicative of pressure of the blood flow thereat.

The inlet pressure sensor 22 and its integral cannula are preferably formed integrally with the blood pump, and a suitable inlet tube or catheter 24 joins the inlet pressure sensor to the left ventricle by being sutured thereto.

The blood pump preferably also includes means in the form of an outlet pressure sensor 26 joined to the outlet side of the pump in flow communication with the aorta by an outlet tube or catheter 28 suitably sutured thereto. The outlet pressure sensor 26 is preferably identical with the inlet pressure sensor 22 and uses the flat diaphragm for accurately measuring pressure of the blood flow in the corresponding cannula.

In the preferred embodiment, the blood pump 20 includes a brushless DC electric motor which powers its impeller, and a suitable battery supply is preferably implanted in the patient for powering the pump. An electrical processor or controller 30 is also preferably implanted in the patient for controlling all operation of the pump. The controller may have any conventional configuration, and is preferably in the form of a digitally programmable microprocessor of sufficiently small size to be integrated directly with the blood pump for minimizing the overall size thereof.

Since the pressures measured by the inlet and outlet pressure sensors 22,26 are absolute pressures, and the blood pressure in the natural heart is a gauge pressure, a reference pressure sensor 32 is preferably also implanted in the patient just below the skin 34, and electrically joined to the controller 30. The reference pressure sensor 32 may have any suitable form, such as those disclosed in U.S. patent application Ser. No. 09/472,708 or Ser. No. 10/160,837, both incorporated herein by reference. The reference pressure sensor 32 detects ambient or external atmospheric pressure on the patient's skin which may be readily subtracted by the controller from the pressure readings of the inlet and outlet pressure sensors for producing gauge pressure readings thereof as desired.

Although the purpose of the blood pump 20 is to assist pumping of the left ventricle 16, the mechanical blood pump is quite different in operation and performance from that of the natural left ventricle, and therefore requires suitable control thereof for effective operation which does not further compromise performance of the already dysfunctional heart.

In accordance with the present invention, the blood pump and its cooperating components described above create an improved system for assisting blood pumping of the left ventricle in an improved method of physiological control of the pump to conform with the natural operation of the left ventricle. As indicated above, the blood pump 20 is joined in parallel flow between the left ventricle and the aorta, and develops a suction inlet pressure which extracts some of the blood from the left ventricle for flow through the pump to the aorta bypassing in parallel the normal flow through the left ventricle itself. However, the left ventricle continues to beat and pump a portion of the total blood flow through the aorta.

Since the blood pump effectively sucks blood from the left ventricle, suction collapse of the left ventricle must be prevented for ensuring continuous blood flow into the arterial system.

In accordance with the present invention, the inlet pressure sensor 22 provides means for measuring inlet pressure P1 of the blood flow to the pump from the left ventricle. The electrical pressure signal from the sensor 22 is suitably provided to the controller 30 by an electrical connection therebetween, and the controller 30 is preferably configured in suitable software for using the inlet pressure for controlling operation of the pump.

Figure 2:
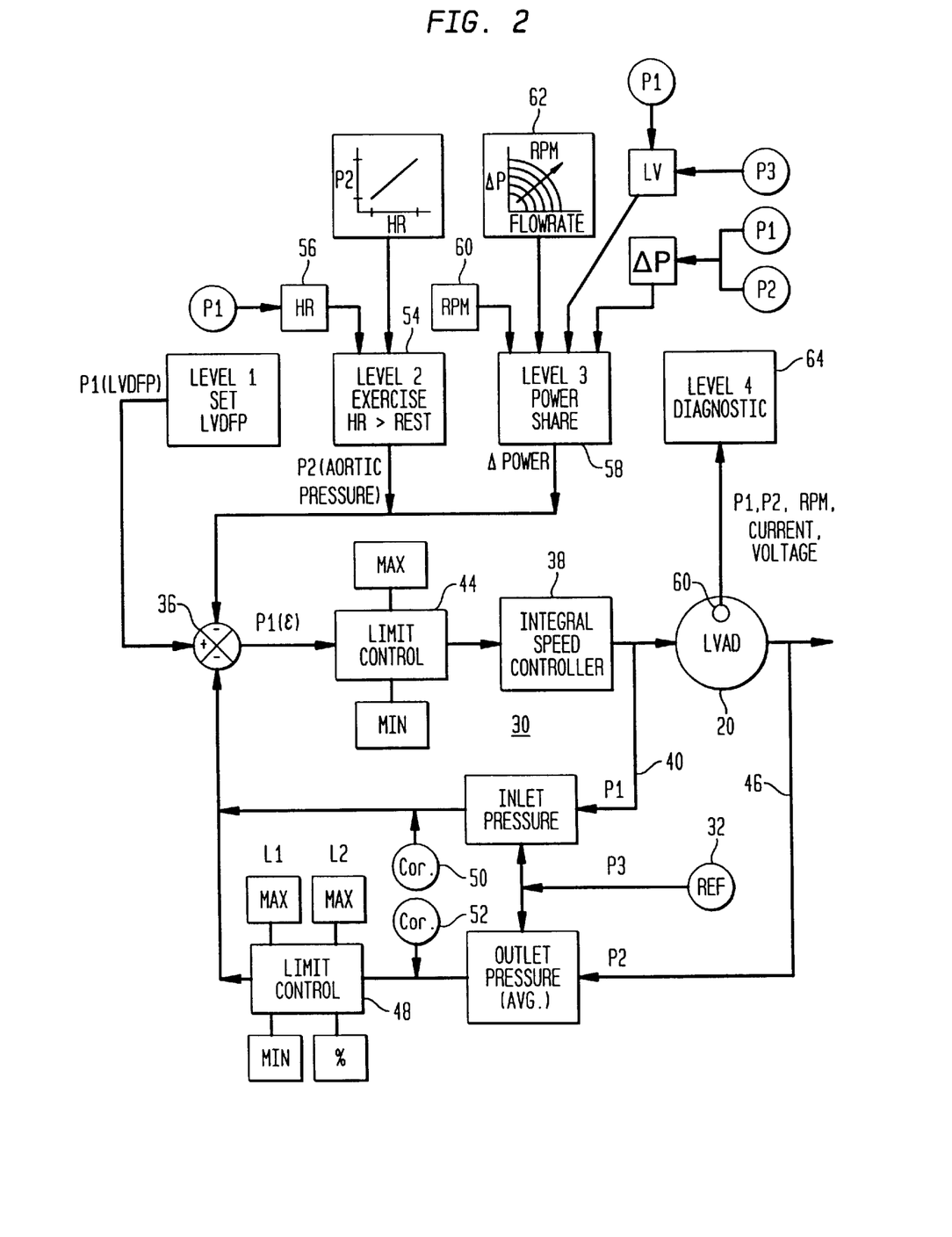
FIG. 2 is a schematic representation of the feedback control for the blood pump illustrated in FIG. 1 in accordance with an exemplary embodiment of the present invention.

FIG. 2 is a schematic representation of the control system implemented in the controller 30 of FIG. 1 preferably using suitable software. The control system illustrated in FIG. 2 includes a conventional summing junction 36 which provides means for comparing the measured inlet pressure P1 from the sensor 22 with a desired or set value thereof to determine a difference or error value therebetween.

The summing junction is operatively joined to the blood pump 20 by a speed controller 38 for the electrical motor thereof, which controls motor operation by rotation of the impeller therein. The rotary speed in revolutions per minute (RPM) of the pump 20 is adjusted in an inner closed loop control 40 using feedback of the measured inlet pressure P1 to minimize the pressure difference with the setpoint at the summing junction 36.

Closed loop feedback control is conventional, and is used in accordance with the present invention for controlling rotary speed of the blood pump based on the measured inlet pressure P1. In a fundamental or first level of pump control, the desired level of the inlet pressure P1 may be suitably set in the control system, and the inner feedback loop 40 is used to control motor speed until the difference or error signal between measured and set pressures is reduced to substantially zero, at which time the measured inlet pressure P1 matches the desired value therefor.

FIG. 1 illustrates schematically a control panel 42 which is suitably operatively joined to the controller 30 for manually setting initial values therein and specifying desired control of the pump. The panel may be hard wired to the controller, but in the preferred embodiment is joined thereto using a suitable telemetry interconnection through the patient's skin for preventing the need for a surgical opening therethrough.

The control panel 42 includes various physician-selected settings for configuring the control system to specific patients, and may also be used for monitoring performance of the system. In accordance with the present invention, the fundamental control parameter is the inlet pressure P1 to the rotary pump which may be used as an approximation or close representation of the Left Ventricular Diastolic Filling Pressure (LVDFP).

If the pump is operated with excessive suction pressure at its inlet, the left ventricle may be driven to collapse under the suction pressure which, of course, interrupts blood flow to the patient and requires prompt correction. By monitoring the inlet pressure to the pump, the inner feedback control loop may be used to ensure that the inlet pressure P1, and associated LVDFP, are not excessively low.

The control system illustrated in FIG. 2 preferably also includes a suitable first limit control or limiter 44 which provides means for limiting measured inlet pressure P1 to a first range preselected by the physician for a particular patient, with the first range having a minimum value for preventing excessive suction or negative pressure leading to collapse of the left ventricle.

The performance of the rotary pump was test evaluated in cooperation with a simulated left ventricle in the form of a flexible sack pneumatically driven in a pulsatile mock loop configuration. A Donavan mock loop, manufactured by MedQuest Products, of Salt Lake City, Utah, USA was used to represent the left ventricle and circulatory system. A centrifugal pump, model EG0024/F, manufactured by Micropump, Inc., of Vancouver, Wash., USA withdrew fluid from the apical connection in the ventricle and returned the fluid to the aorta to represent a generic heart assist pump. This pump maintains its impeller speed proportional to a control voltage signal that it receives.

The following Table 1 summarizes the results of thirteen test runs in which the pump inlet pressure setpoint was varied from +10 to −2 mm Hg. The mock loop was configured to simulate left ventricle performance using a 100 mm Hg pneumatic driving pressure applied at 60 beats per minutes (BPM) through a 30% diastole cycle.

TABLE 1

| LVDFP P1 (mm Hg) | Mean Arterial Pressure P2 (mm Hg) | LVAD Flowrate (liters/minute) | LVAD Speed (RPM) |
|---|---|---|---|
| 10.0 | 52 | 4.2 | 2490 |
| 9.0 | 58 | 5.0 | 2720 |
| 8.0 | 64 | 5.7 | 2920 |
| 7.0 | 68 | 6.0 | 3080 |
| 6.0 | 74 | 6.7 | 3250 |
| 5.0 | 79 | 7.2 | 3420 |
| 4.0 | 86 | 7.7 | 3600 |
| 3.0 | 93 | 8.1 | 3780 |
| 2.0 | 102 | 8.7 | 4010 |
| 1.0 | 109 | 9.1 | 4170 |
| 0.0 | 116 | 9.5 | 4320 |
| −1.0 | 124 | 9.8 | 4490 |
| −2.0 | 136 | 10.4 | 4710 |

Table 1 indicates that as the pump inlet pressure P1 decreases, the pump outlet pressure P2 increases along with an increase in pump flowrate and rotary speed of the impeller.

The physician may use the known performance of the particular blood pump being used for controlling its operation for specific patient's needs.

For example, the control panel 42 illustrated in FIG. 1 permits the physician to set the desired inlet pressure P1 for the pump, as well as the corresponding first range for the measured inlet pressure P1, which is +10 to −2 mm Hg, which corresponds with the full range in Table 1, for example. The first level of feedback control provided in the inner loop 40 may then be used to control operation of the pump to achieve the desired setpoint for the inlet pressure P1, with the panel 42 illustrated in FIG. 1 showing the actual measured value of the inlet pressure P1 in the corresponding circular indicator. In contrast, the square indicators are used for the various physician programmable values in the control system.

The control panel 42 illustrated in FIG. 1 also includes a visual monitor which displays the real time performance of the measured inlet and outlet pressures P1,P2 and pump speed in RPM. The exemplary display indicates Level-1 performance in which the RPM gradually increases for correspondingly increasing the outlet pressure P2 of the pump as the inlet or filling pressure P1 decreases, as represented by the minimum or valley portion of the cyclical performance thereof. In the first level (1) control, the measured inlet pressure P1 reached the 3.0 mm Hg desired setpoint value thereof in testing.

For Level-1 control, the preselected first range of inlet pressure P1 also includes a maximum value of the inlet pressure so that the right heart, i.e. right atrium and ventricle, is not overburdened by excessive pressure in the left atrium whose pressure is reflected in the filling pressure of the left ventricle.

Table 1 indicates that the higher values of inlet pressure P1 correspond with lower values of the outlet pressure P2, flowrate, and pump speed. Since the rotary pump 20 is a through-flow device without the complexity of check valves therein, the flowpath through the pump necessarily bypasses the left ventricle to the aorta in parallel flow therewith. Should the rotary pump be operated too slowly, with the output of the left ventricle being greater than that of the pump, the blood from the aorta may flow back through the pump toward the left ventricle in retrograde flow. Accordingly, the setpoint on inlet pressure P1 may be selected by the physician within the selected first range to avoid retrograde flow.

Accordingly, the physician has the ability to specify the desired range of operation of the measured inlet pressure P1, including both minimum and maximum values thereof as desired for ensuring proper operation of the pump in conjunction with the beating left ventricle.

As indicated above, the control system preferably also includes means in the form of the outlet pressure sensor 26 illustrated in FIG. 1 which are operatively joined to the controller 30. In this way, the outlet pressure sensor may be used for measuring pressure of the blood flow from the pump to the aorta in parallel with pumping of the blood from the left ventricle to the aorta.

As illustrated in FIG. 2, the controller 30 is suitably configured for adjusting speed of the pump in an outer closed loop control 46 using feedback of the measured outlet pressure P2 for maintaining the outlet pressure in a second range preselected by the physician. The outer loop 46 preferably operates in conjunction with the inner loop 40, with feedback of the measured inlet pressure P1 being used for maintaining the measured inlet pressure in the first preselected range.

The control system illustrated in FIG. 2 also includes a suitable second limit control or limiter 48 configured for effecting the preselected second range of outlet pressure P2, with the control panel 42 illustrated in FIG. 1. including corresponding indicators for manually selecting the upper and lower limits on the outlet pressure range, with 110 and 70 mm Hg being illustrated for example, and corresponding with intermediate values of the outlet pressures listed in Table 1.

As shown in FIG. 2, the outer feedback loop control 46 is configured in a loop to the common summing junction 36 for adjusting the inlet pressure P1 within its first range as implemented by the first limiter 44 for maintaining the outlet pressure P2 within its second range as implemented by the second limiter 48. In this way, both the inlet pressure P1 and outlet pressure P2 may be controlled within physician specified ranges, with primary Level-1 control being based on the inlet pressure P1.

In the preferred embodiment, the inlet pressure P1 is measured over a period of at least one full heartbeat cycle, and consists of the minimum value during that period. In this way, the measured inlet pressure corresponds directly with the desired LVDFP in the left ventricle, and is a close approximation thereof If desired, the control system illustrated in FIG. 2 may include suitable means 50 for correcting the measured inlet pressure P1 to conform with the diastolic filling pressure inside the left ventricle. Since the inlet pressure sensor 22 is not located directly inside the left ventricle, but closely adjacent thereto, a small difference in pressure therebetween exists. A suitable correction for this difference to better conform the measured inlet pressure P1 to that inside the left ventricle may be effected based on empirical data, or analysis.

Similarly, the outlet pressure sensor 26 is located closely adjacent to the aorta 18 but not inside the aorta. Accordingly, the pressure measured by the outlet pressure sensor is a close approximation to the arterial pressure inside the aorta, and may be similarly corrected by introducing corresponding means 52 in the outer feedback loop 46 of Level-1. The measured value of the outlet pressure P2 may be suitably corrected using empirical data or analysis, as indicated above for the inlet pressure sensor, for more accurately conforming with the arterial pressure inside the aorta.

In this way, the two pressure sensors 22,26 provided with the blood pump 20 may be used for closely approximating the actual pressures inside the left ventricle 16 and inside the aorta 18.

Furthermore, since blood pressure is a gauge pressure in practice, the reference pressure sensor 32 illustrated in FIGS. 1 and 2 is preferably used for measuring the atmospheric reference pressure P3 at the patient's skin 34, which is then used for correcting the measured inlet and outlet pressures P1,P2 to gauge pressure. The reference pressure P3 is simply subtracted in the controller from the measured values of the inlet and outlet pressures P1,P2 to provide gauge values therefor for better matching the physiological control of the natural heart.

The fundamental operation of the Level-1 control is to maintain the left ventricular diastolic filling pressure within a suitable range for effective filling performance of the left ventricle. The filling pressure is the instantaneous minimum pressure per heart cycle.

However, the output of the heart must have sufficient blood flow for proper operation of the human body. Correspondingly, the mean arterial pressure in the aorta is indicative of heart performance, and therefore the control system illustrated in FIG. 2 is configured for using a suitable average of the measured outlet pressure P2 in the control of the pump. As illustrated in the monitor of FIG. 1, the instantaneous trace of the outlet pressure P2 is periodic with beating of the heart, but has an average value which may be conventionally determined in the control system for use in controlling the pump.

And, the first level control is preferably implemented as an integral proportional feedback control for maintaining the minimum inlet pressure P1 within the physician selected range.

Since the outer loop 46 of the Level-1 control is configured for keeping the arterial pressure P2 within the desired programmed limits, it preferably has a slower response time than the inner control loop 40 which uses solely the minimum or diastolic filling pressure portion of the measured inlet pressure P1.

The control system illustrated in FIG. 1 preferably also includes a second level of control typically associated with the patient undergoing exercise and requiring additional blood flow. Level-2 control is indicated schematically by the reference numeral 54 in FIG. 2 and is readily incorporated into the control system using additional software.

As additionally shown in FIG. 1, the physician may specify a resting heart rate (HR) for the patient in terms of beats per minute (BPM). And, as shown schematically in FIG. 2, means 56 are provided for measuring or determining the heart rate of the patient's heart which is used for initiating the Level-2 control. When the measured heart rate is greater than the specified resting heart rate, the second level control 54 is effective for increasing speed of the blood pump to correspondingly increase the outlet pressure P2, and thereby provide more blood flow for meeting the increased demand therefor during exercise.

When Level-2 control is activated above the resting heartbeat, the second range of outlet pressure P2 is suitably suspended in the second limiter 48, with the second range being suitably replaced by a different preselected third range of the outlet pressure P2 as illustrated schematically in FIG. 2 at the second limiter 48.

As indicated above, the second range of outlet pressure P2 under Level-1 control includes preselected maximum and minimum values of the outlet pressure. However, for the second level of control, the third range, which replaces the second range, includes a different preselected maximum value of the outlet pressure P2 which is preferably higher than the maximum value in the non-exercise Level-1 control, and a preselected maximum percent (%) increase of the outlet pressure above the outlet pressure at the resting heart rate. Correspondingly, the Level-2 control also includes a preselected maximum permitted increase in the heart rate, all of which values may simply be programmed into the controller at the control panel illustrated in FIG. 1 with corresponding square indicators illustrated therefor.

In the preferred embodiment, the outlet pressure P2 in Level-2 control is increased linearly in response to increase in the measured heart rate as derived from the physician selected third range of outlet pressure parameters. For example, the physician selects the maximum permitted outlet pressure P2 and the maximum percent increase in outlet pressure above the outlet pressure at the specified resting heart rate. And, the physician specifies the maximum permitted increase in heart rate.

Since the outlet pressure at the specified resting heart rate is variable, the actual value thereof is not known until it is measured in situ for a particular patient at the specified resting heart rate. Once the outlet pressure of the specified resting heart rate is measured by the outlet pressure sensor 26, the Level-2 control may then be used to determine or calculate the permitted linear increase thereof within the specified controlling parameters as represented by the HR-P2 graph illustrated in FIG. 2.

In this way, Level-2 control is initiated above the resting heart rate for increasing the outlet pressure P2 from the pump by adjusting the setpoint of the inlet pressure P1 at the common summing junction 36. And, the Level-2 control during exercise includes new limits on the outlet pressure P2 specific to exercise, as opposed to the previous limits imposed by the second limiter 48 during Level-1 control at rest. The blood pump 20 is then operated for increasing the outlet pressure P2 to meet the increased demands of patient exercise, while still controlling the blood pump within the specified range of inlet pressure P1.

The means 56 for measuring heart rate are illustrated schematically in FIG. 2 and are preferably effected by measuring the periodic pulses in the measured inlet pressure P1 which corresponds with beating of the heart. As shown in the monitor of FIG. 1, the measured inlet pressure P1 has a periodic pulse corresponding with the heart rate or beating of the heart. The controller may therefore be configured with suitable software for analyzing the inlet pressure signal to discern the beating thereof as represented by the periodic pulses and provide the corresponding heart rate in BPM. In this way, a separate heart rate sensor is not required since suitable information is already available from the instantaneous measuring of the inlet pressure P1.

A third level of control 58 is illustrated schematically in FIG. 2 and includes suitable means 60 for measuring rotary speed of the pump as expressed in RPM. It is noted that the pump 20 is conventional and typically includes an electrical outlet line that provides a speed signal for the pump using suitable measuring means integrated in the pump itself. Additional outputs for the pump may include the voltage and electrical current for the motor thereof.

The third level control 58 further includes means for determining the differential (delta) pressure between the measured outlet and inlet pressures, P2-P1. And then, the flowrate through the pump may be calculated or determined using predetermined performance curves 62 for the pump based on the measured speed and pressure differential.

As indicated above, typical rotary pumps have performance curves which plot differential pressure across their outlets and inlets versus flowrate, with different curves for different speeds of the pump impeller. By measuring differential pressure and pump speed, the corresponding flowrate may be readily determined.

The Level-3 control is additionally configured for determining pumping power for the blood pump 20 which is the product of the pressure differential and the flowrate. In this way, output power from the pump 20 may be determined, and expressed in watts as indicated in the monitor illustrated in FIG. 1.

In the preferred embodiment illustrated in FIG. 2, the Level-3 control is also operatively joined to the common summing junction 36 for correspondingly adjusting speed of the pump using the same inlet pressure P1 control parameter for controlling pumping power of the pump within the other constraints of the Level-1 and Level-2 controls. Although the fundamental control parameter is inlet pressure P1, both the outlet pressure P2 and pump power may be secondarily controlled within the permitted ranges of inlet pressure P1 and outlet pressure P2 as selected by the physician.

As shown schematically in FIG. 2, the Level-3 control 58 preferably also includes means for determining pumping power for the left ventricle, and then adjusting pumping power of the blood pump 20 to correspondingly share pumping load between the pump and the left ventricle.

Pumping power of the left ventricle may be approximated by using the pressure difference across the ventricular wall as calculated by subtracting the ambient atmospheric pressure P3 from the internal ventricular pressure as approximated by the pump inlet pressure P1. The flow through the ventricle to the aorta is approximated by the flow through the pump 20 as calculated above. The power for the left ventricle is then calculated as the product of this differential pressure and flow, and is determined primarily only during the systolic pumping phase because during the diastolic phase the left ventricle is mostly passively filled.

The monitor illustrated in FIG. 1 indicates calculated power for the left ventricle and blood pump for an exemplary load division. The control system may be configured in any suitable manner to further modify the inlet pressure P1 control signal for achieving desired load sharing within the permitted ranges of inlet pressure and outlet pressure.

It is noted that the three levels of pump control illustrated in FIG. 2 all share the common summing junction 36 for adjusting performance of the primary Level-1 feedback control loop 40 for primarily controlling the inlet pressure P1, and secondarily controlling outlet pressure P2 during rest in Level-1 and during exercise in Level-2, and pump power or load sharing in Level-3 within the programmed limits of inlet and outlet pressures.

The control system illustrated in FIG. 2 may also include a fourth level of control 64 specifically configured for monitoring the inlet and outlet pressures P1,P2, and performance of the pump 20 to diagnose abnormalities therewith. All of the various operating parameters of the pump and associated pressure sensors may be monitored and temporarily stored in suitable memory for use in diagnostic monitoring of system performance for comparing present performance with past performance to diagnose any abnormalities which may develop.

The function for the Level-4 diagnostic mode is to monitor for any changes that may lead to LVAD support failure. In one potential failure mode, protein deposition may form on the pumping surfaces and lead to an increased motor current. This increase in motor current may not result in a change in the LVAD flowrate.

This trend in pump operating characteristics may be detected by monitoring the trend in the two independently calculated flowrates: (1) the flowrate based on the pressure difference across the pump, and (2) the flowrate estimated from the motor current. The flowrate calculation based on pressures is accurate providing the pump characteristics do not change. It is anticipated that the protein deposition example is most likely to occur in areas of low flow rather than in areas of high flow that determine the pressure versus flow characteristics of the LVAD.

Note that it may be possible to measure key values of the operating characteristics during an in vivo pressure calibration procedure, i.e., measure the no-flow pump head pressures. Also note that the flow calculation based on pressure is not significantly influenced by viscosity over the range of expected viscosities.

In another failure mode, the wires connecting the pressure sensors may break resulting in abnormal pressure signals and abnormal flowrate calculations. A histogram of past pressure signal levels and past flowrates may detect this failure mode. In case of a pressure sensor failure, the motor current may be used as a backup parameter to control the pump. Prior to the pressure sensor failure, correlation of the motor current history with the corresponding pump speed and pump pressures histories may result in a useable operating relationship.

The various levels of control of the heart pump 20 introduced above permit a physician to tailor pump performance to individual patient condition and needs. These levels of control are arranged in a preferred hierarchy fundamentally using the inlet pressure P1 between the heart and the pump for effective physiological control of the pump to complement natural performance of the heart.

The primary strategy for the multiple-level control algorithms used to implement the hierarchical control is to use the physiologic information provided by the pressure sensors to mimic the patient's natural physiologic control system. In particular, the strategy is to fulfill the following three basic heart functions:

1) BALANCE OUTFLOW WITH INFLOW

Level-1 contains the primary control loop that regulates the left ventricle diastolic filing pressures within an acceptable operating range selected by the physician. By controlling the left ventricle diastolic filling pressures on a beat-to-beat basis, the resulting LVAD speed profile maintains a flow balance such that the average LVAD pumped flow together with the average native heart output flow is equal to the average return flow to the left heart.

By controlling the diastolic filling pressure, the physiologic control algorithm is simulating the control initiated by the stretch receptors in the left ventricle in accordance with the conventional Frank-Starling principle.

2) MAINTAIN ADEQUATE ARTERIAL PRESSURE

Level-1 contains the secondary control loop that regulates the mean arterial pressure within acceptable operating range. By controlling the range of the mean arterial pressure, the physiologic control algorithm is simulating the control initiated by the baroreceptors in the arterial system.

3) MAINTAIN ADEQUATE CARDIAC OUTPUT DURING EXERCISE

The principle for the Level-2 physiologic control algorithm is the use of heart rate as physiologic indicator based on sympathetic nervous system regulation of the circulation system during exercise or stress. The blood flow to exercising muscles increases much more as a function of increased blood pressure than as a function of heart rate alone. The typical increase in mean arterial pressure is up to approximately 30% during exercise.

However, because the left ventricle is compromised, the LVAD patient is not able to increase his/her heart output in response to exercise. By controlling the increase in mean arterial pressure during exercise, the physiologic control algorithm is simulating the control of the sympathetic nervous system.

The method disclosed above may be used to control a heart assist pump using blood pressure as a physiologic control variable. Two pressure sensors are used to provide blood pressure inputs for this control algorithm. They are typically mounted on the inlet and outlet of the heart pump, such as a Left Ventricular Assist Device.

The direct inputs to the physiologic control algorithm preferably include the LVAD inlet pressure and the LVAD outlet pressure. And, additional inputs may also include the LVAD motor speed and the LVAD current.

Another, indirect, input is the heart rate, which can be derived from the LVAD inlet pressure. The output of the physiologic control algorithm is the LVAD speed control voltage. The hierarchy of the inputs and their allowable ranges defines the control space for the above inputs. The physiologic control algorithm functions are preferably divided into four Levels associated with physiological control of the heart.

Level-1 is the primary control loop that regulates the left ventricle diastolic filling pressures within an acceptable operating range selected by the physician. By controlling the left ventricle diastolic filling pressures on a beat-to-beat basis, the resulting LVAD speed profile maintains a flow balance such that the average LVAD pumped flow together with the average native heart output flow is equal to the average return flow to the left heart.

The Level-2 and Level-3 control algorithms provide additional outer feedback to modulate the Level-1 primary loop feedback control. The Level-2 control algorithm tries to increase the arterial pressure by increasing pump speed based on increased heart rate. Increased arterial pressure results in increase blood flow to those muscle tissues with dilated arterioles, e.g., during exercise. The increase in pump speed can only occur if the left ventricle diastolic filling pressure is maintained within its acceptable range.

Level-3 control algorithm tries to control the pump speed so as to adjust the hydraulic pump power relative to the left ventricular hydraulic power. Again, any change in pump speed can only occur if the left ventricle diastolic filling pressure is maintained within its acceptable range. Preferably only one higher mode Level, e.g., Level-2 or 3 may be selected at any one time.

To maintain stability to the overall system, the response time for Level-1 is faster than the response times for Level-2 and Level-3. Level 4 is a diagnostic mode that detects abnormal events or abnormal trends in pump and cannulae performance or in left ventricle performance.

The Level-1 input control space variables are defined as follows. The primary control variable measures diastolic filling pressures derived from the LVAD input pressure sensor. The secondary control variable measures average arterial pressure derived from the LVAD output pressure sensor.

The basic principle for the Level-1 physiologic control algorithm is the use of left ventricular filling pressures to mimic the functional principle of the Frank-Starling mechanism applied to the left heart. Thus within physiological limits, the left heart and the LVAD pump all the blood received into the left ventricle without allowing excessive damming or excessive suction that can lead to collapse of the left ventricle.

The primary controlling parameter for this Level-1 algorithm is the diastolic pressure during the left ventricular pressure cycle. The minimum diastolic pressure may be used rather than the end diastolic pressure to prevent ventricular collapse because the LVAD inlet is continuously pumping from the apex of the left ventricle.

The rules defining Level-1 control are as follows:

The primary rule states that the primary control variable must stay within a range selected by the physician.

The secondary rule states that the secondary control variable may stay within non-exercise range selected by the physician providing the primary rule is not at a boundary.

The tertiary rule states that the primary control variable may stay at a fixed value selected by the physician provided the primary rule and the secondary rule are not at their boundaries. The tertiary rule may evolve into an adaptive strategy for selecting a relatively optimal diastolic filling pressure that may vary with time based on the patient status. Based on preliminary observations, optimal value may be defined as the minimum area in the two-parameter control space, i.e., minimize any localized instability in the primary versus secondary parameter control space in a given time.

The Level-2 input control space variable is heart rate as preferably derived from the input pressure sensor. The principle for the Level-2 physiologic control algorithm is the use of heart rate as physiologic indicator based on sympathetic nervous system regulation of the circulation system during exercise or stress.

The blood flow to exercising muscles increases much more as a function of increased blood pressure than as a function of heart rate alone. The typical increase in mean arterial pressure is up to approximately 30% during exercise. However, because the left ventricle is compromised, the LVAD patient is not able to increase his/her heart output in response to exercise. Therefore the heart rate signal is used to increase pump speed resulting in higher arterial pressure.

The physician makes this selection of the actual relationship, e.g., linear increase in mean arterial pressure as heart rate increases (with limit values on mean arterial pressure and heart rate). The Level-2 control monitors the arterial pressure and compares it with the desired arterial pressure that is based on the measured heart rate and derived from the linear relationship mentioned above between heart rate and mean blood pressure. The difference signal multiplied by a constant is then used as a negative input to the Level-1 primary control variable. The interaction of Level-2 with Level-1 is shown schematically at the summing junction 36 in FIG. 2.

The Level-3 input control space variables use measured pressures and pump speed to determine LVAD and left ventricle hydraulic pumping power in watts. The function of the Level-3 control algorithm may be to control the hydraulic output power produced by the LVAD to a not-to-exceed value or a fixed percentage of total hydraulic work that is predetermined by the physician to prevent the left ventricle from work overload.

Another option for controlling the pump power may be to fix the left ventricle power at a constant level selected by the physician. The Level-3 control algorithm may also be used by the physician to temporarily decrease the hydraulic output power produced by the LVAD during controlled exercise periods. This function may be used to condition the left ventricle.

Another application for Level-3 is the ability to monitor the left ventricular power during controlled treadmill exercises. This function permits the physician to monitor the recovery of the heart muscle or its deterioration.

Note that the left ventricular power calculation is only accurate when the aortic valve does not open during LVAD assist. Opening of the aortic valve may be detected by the presence of the dicrotic notch in the arterial waveform. The dicrotic notch results from the back-flow created pressure during closing of the aortic valve.

The LVAD pumping power is the pressure differential (outlet minus inlet pressure) multiplied by the estimated flowrate. The estimated flowrate is obtained using the pressure differential across the LVAD, the rotary speed, and the LVAD pressure versus flow characteristics as a function of the control voltage input. Note that the fluid flowrates for a centrifugal pump are primarily related to the momentum rather than the viscosity, so that physiological changes in blood viscosity may be ignored.

The Level-3 control is an outer loop control that modulates the control signal to the Level-1 control loop. For example, the difference in power between the desired value and the calculated value is multiplied by a given constant and then may be used as a negative input to the Level-1 primary control variable. The interaction of Level-3 with Level-1 is shown at the summing junction 36 in FIG. 2.

The Level-4 diagnostic capability is described above, and is effective for monitoring the various signals generated in the control system.

The goal of the control system is to permit a cardiac challenged patient to return to home or work with an improved level of activity and quality of life. The primary aim of the physiologic controller is to prevent the heart from being overstressed while at the same time to condition the heart to encourage partial recovery of heart function. The secondary aim of the physiologic controller is to provide a non-invasive method for the physician to assess heart function via passive and active stress testing and assess functional integrity of the pump and cannula.

The objectives of the physiologic control algorithms are the following:

1) DEMAND MODES: The Level-1 mode for the physiologic controller algorithm adjusts the impeller speed so that the blood pump meets the patient's flow requirements related to the capability of the native heart. The primary pressure input to the physiologic controller is the left ventricular diastolic filling pressure (LVDFP) that may be derived from the pump input pressure sensor signal. The secondary pressure to the physiologic controller is the aortic pressure (AoP) that may be derived from the pump output pressure sensor signal.

The primary pump speed control rule is to maintain the LVDFP at a desired selectable value within selectable limits. The secondary pump speed control rule is to maintain the AoP within a desired selectable range. If the AoP approaches a limit, then the LVDFP value is allowed to change value within its selectable range. Thus the primary LVDFP range takes precedence over the secondary AoP range.

The Level-2 mode for the physiologic controller algorithm adjusts the impeller speed (always staying in the Level-1 range for the LVDFP) so that the AOP increases with the heart rate as derived from the input pressure sensor. The controller 30 preferably also include a left ventricular collapse detection algorithm and a retrograde flow detection algorithm. Note that flow can be calculated using the pressure differential across the blood pump 20 in conjunction with the rotary speed and the pressure versus flow characteristics of the pump.

2) CONDITIONING MODES: The Level-3 mode for the physiologic controller algorithm adjusts the impeller speed so that the pump may provide conditioning of the native heart by providing programmed periods of time where the pump reduces its hydraulic power.

The physiologic controller algorithms use the pressure input and output measurements to calculate the pump hydraulic power as well as the native heart hydraulic power (when the aortic valve is closed). The physician can program the Level-3 mode to correspond to a passive conditioning mode or active conditioning mode. The Level-3 mode is always constrained to be within the boundary of the Level-1 primary parameter range.

3) PATIENT DIAGNOSTIC MODE: The physician may monitor the native heart power and pump power (as calculated by the physiologic controller algorithm) to monitor the patient during controlled exercises on the treadmill. The Level-4 diagnostic mode permits the physician to periodically measure trends in recovery or deterioration due to disease progression.

4) PUMP AND CANNULAE DIAGNOSTIC MODE: The pressures measured at the inlet and outlet of the pump as well as the flow calculation derived from the pressure measurements provides primary diagnostic capability for detecting flow blockages. A pump diagnostic method for measuring performance changes of the blood pump 20 is to compare the flow derived from the pressure measurements with the flow derived from the motor current. It is anticipated that trend data may provide an early warning of impending failure.

The pump and cannula diagnostic mode is designed to detect abnormal pressures such as those generated by flow blockages or by defective subsystems. The control and diagnostic algorithms have been tested via simulation of these abnormal conditions on the mock loop.

For the first level control, an integral proportional pump control algorithm uses as the control input the LVDFP as represented by the measured inlet pressure P1, preferably the corrected gauge pressure. The controller compares the measured inlet pressure to a setpoint and uses the difference as an error signal.

The error signal is integrated with respect to time and multiplied by a suitable value K. In equation form, the basic control is: $d/dt(Flow)=K*(inlet\ pressure-setpoint\ pressure)$; that is, the rate of change in flow pumped through the blood pump is calculated by multiplying K times the error.

In one embodiment, K is a constant. A good value for this constant has been experimentally found to be approximately K=0.1 liter/min/sec/mmHg. For example, if the error signal indicated that the inlet pressure was too high by 10 mmHg, the flowrate would be increased by 1 liter/min each second to correct it.

In another embodiment, K is a function of the error. In this embodiment K is larger when the error is smaller. In particular, K is larger when the error is less than zero. For example, there may be two values of K: K+ and K−. The positive value K+ is used when the error is positive and the negative value K− is used when the error is negative. K− should have a value smaller than K+.

The effect of the higher value of K– is that the system reacts more quickly to low pressures in the ventricle to avoid the dangerous condition of suction and collapse of the ventricle. For example, if K–=–0.2 liter/min/sec/mmHg, and the inlet pressure were too low by 10 mmHg, the flow would decrease by 2 liter/min each second. Low pressures in the ventricle signal imminent collapse of the ventricle. The more rapid reduction in pumping rate in response to low pressures would make it more likely that the collapse of the ventricle would be avoided.

The effect of the lower value of K+ is that the system reacts more slowly to high pressures in the heart. There is no urgency to correct the inlet pressure when it is too high. For example, for the lower value of K+=0.02, if the pressure were too high by 10 mmHg, the pumping rate would increase more slowly, only by 0.2 liter/min each second. The slower rate of increase would prevent overshoot and stabilize the overall control algorithm.

The net result of this combination is that the composite algorithm is fast enough to be safe and slow enough to be stable.

The usefulness of such a fast algorithm was demonstrated on tests on the mock loop describe above. The ventricle component of the mock loop was brought from the normal, uncollapsed condition to the collapsed condition by suction caused by the pump pumping too hard.

The collapse could be done repeatably by increasing the pump speed to deliver approximately 10 liters per minute. Furthermore, a fluttering instability reported in calf experiments has been repeated in this experimental setup.

Fluttering instability of the left ventricle may be represented by exposing the ventricle to suction pressures between –50 mmHg and –250 mmHg, with oscillation between these two pressures. These experiments only approximate the quantitative pressures expected in a real heart, however, it appears that the qualitative mechanism of the instability has been identified in these experiments.

The instability appears to follow this sequence:

1) An excess pumping speed causes suction pressures in the ventricle;
2) The ventricle walls close together, and partially block off the pump inlet cannula;
3) A large, negative pressure spike appears in the ventricle, caused by:
   a) The pump dead-ending against the flow cutoff at the inlet, and
   b) The momentum of the column of blood coming to a sudden stop.
4) After stopping, the column of fluid bounces backward, being pulled back by the large negative pressure spike in the ventricle;
5) The backward motion reopens the closed ventricle, allowing forward flow resume; and
6) Steps 1–5 repeat.

A controller is needed to avoid the excess pumping speed that causes the suction pressure in step 1. If for some reason, the suction in step 1 does occur, the controller should be able to react quickly enough to avoid step 2, the ventricle collapse. This shows the importance of both controlling the pressure and responding quickly to reduce pump speed in response to suction in the ventricle.

A method has also been developed to use pressure measurements to monitor the hydraulic power produced by the ventricle. Hydraulic power of the heart is the pumping power that actually goes into the blood, and it is a measure of how hard the heart is working. It is pressure times the volume flowrate.

For the heart, the relevant pressure is the difference between ventricular pressure (inside the heart) and the pressure outside of the heart muscle wall. This pressure is a measure of how hard the heart is squeezing. The flowrate is a measure of how much volume the heart is squeezing. The product of flowrate times pressure is a measure of how much hydraulic power the heart is producing.

Note that only the flow that goes through the pump is being measured. If the ventricle pumps faster than the pump, the excess flow goes out of the aortic valve in the normal manner, and this excess flow is not accounted for in the calculation of hydraulic power. In such cases, this method of calculating ventricular power may be considered as an estimate of the minimum power.

In this calculation of heart power, in one method only the power during the systolic phase is calculated. The systolic phase can be defined as the portion of the pumping cycle in which the ventricular pressure is above a measured diastolic level, e.g., 8 mmHg. This eliminates the calculated power in the diastolic phase, during which the ventricle is filling.

In conjunction with the hydraulic power calculation of the heart, the power calculation of an implanted heart pump can be calculated. The formula for the hydraulic pump power is the product of the difference in pressure between the pump outlet and inlet times the flowrate through the pump. In contrast to the heart power, the pump power is valid throughout the pumping cycle.

When calculating both the heart power and pump power, an additional calculation can be done to compare the two powers. This is useful clinically to display to the cardiologist the relative power produced by the heart and by the pump.

The control panel 42 illustrated in FIG. 1 may be used to display on the monitor thereof any desired information, including flow through the blood pump. Calculated flow through the pump may be based on the predetermined pump performance curves of pressure vs. flowrate as a function of pump speed. Calculated flow can be compared to calculations of the flow by other means, or can be compared with actual output of a flow meter specifically provided therefor. In this way pumping performance of the pump may be monitored.

A comprehensive control panel 42 is shown in part in FIG. 1. The panel includes a suitable monitor to display time dependent traces of the pump inlet pressure, the pump outlet pressure, pump speed for the implanted pump. Or, it can be used to display additional information, including that associated with lab testing, and including the pump control signal, the flowmeter, and computed flow. The control panel also allows selection of manual control (constant pump speed), Level-1 control enabled, Level 1 & Level 2 combined, or Level 1 & Level 3 combined.

The hierarchical algorithms disclosed above have been developed for enhanced physiologic control and monitoring of blood pumps using pressure inputs. Pressures are measured at pump inlet and outlet using suitable pressure sensors.

The algorithms have been tested using the Donavan circulatory mock loop setup, a generic rotary pump, and LabVIEW software. The hierarchical algorithms control pump speed using pump inlet pressure as a primary independent variable and pump outlet pressure as a secondary dependent variable.

Testing has confirmed that hierarchical control algorithms based on feedback from pressure sensors can control the speed of the pump to stably maintain ventricular filling pressures and arterial pressures. Monitoring algorithms based on pressure inputs are able to approximate flowrate and hydraulic power for the pump and the left ventricle.

The algorithms are intended to provide a definitive method for physiologic control to prevent excessive negative pressures in the ventricle, to avoid retrograde flows in the pump, and to auto-regulate the pump impeller speed to maintain arterial pressures appropriate for patient exercise level and perfusion needs.

The algorithms may also use the pressure sensor inputs for advanced monitoring of heart assist devices. The algorithms convert measured values of pressure into calculated values of flowrate and the hydraulic power imparted to the blood by both the pump and the left ventricle. The calculated quantities may be used to detect and monitor abnormal LVAD performance, abnormal ventricular function, and trends in ventricular function and LVAD performance.

The pressure sensors used in the supporting experiments were developed and manufactured by APEX Medical, Inc. of East Walpole, Mass., USA. The basic sensor, referred to as the APEX Pressure Sensor (APS), is both patented and described in a previously published article.

The APS uses a pressure-sensing diaphragm that can be integrally built into the wall of any titanium pump or inlet cannula. The pressure-sensing tube can be made with an inside diameter the same as any LVAD inlet cannula. Mounted on the pressure-sensing diaphragm is a molecularly bonded, thin-film strain gage, whose strain measuring elements are located at the points of highest tensile and compressive strain.

A Millar MPC-500 MikroTip catheter pressure sensor, made by Millar Instruments of Houston, Tex., USA was placed adjacent to the APS for comparison measurement. The flow was measured by a model T110 ultrasonic flow meter, manufactured by Transonic Systems, Inc., of Ithaca, N.Y., USA. And, the Donavan mock loop was used to represent the left ventricle and circulatory system.

The control algorithms used to drive the control module were written in LabVIEW (Laboratory Virtual Instrument Engineering Workbench) version 5.1 software. A DAQPad M10-16XE-50 data acquisition and control module collected the proportional voltage signals produced by the pressure sensors and the flow meter, and generated a proportional voltage output for the pump. Both of the above are sold by National Instruments, Inc. of Austin, Tex., USA.

The primary goal of Level 1 control is to maintain the Left Ventricular Diastolic Filling Pressure (LVDFP), or Filling Pressure, within a physician programmable range. An integral control algorithm was implemented with pump inlet pressure, which is representative of LVDFP, as the input and pump speed control signal as the output. The purpose of this Level-1 goal is to mimic the functional principle of the Frank-Starling mechanism applied to the left heart.

The secondary goal of Level-1 is to optimize the LVDFP within the physician programmed range such that the arterial pressure is within the physician programmed target range. Thus, within the physician programmed LVDFP range and mean arterial pressure target range, the overall goal is to have the left heart and the rotary assist device pump all the blood incrementally received into the left ventricle without allowing excessive damming or excessive suction that can lead to collapse of the left ventricle.

The goal of Level-2 control is to maintain the pump average outlet pressure, which is representative of mean arterial pressure, at a target value during elevated ventricular pulse or heart rate levels such as during exercise. This target value is based on the amount of increase of the pulse rate above a resting level threshold. The linear relationship between heart rate above a threshold and increased mean arterial pressure is programmed by the physician to be patient specific.

When Level-2 control is activated and the pulse rate is at or below this threshold, the Level-2 control algorithm is dormant and has no input on the Level-1 control algorithm. Level-2 uses the heart rate as a physiologic indicator based on sympathetic nervous system regulation of the circulation system during exercise or stress.

The blood flow to exercising muscles increases much more as a function of increased blood pressure than as a function of heart rate alone. The typical increase in mean arterial pressure is up to approximately 30% during exercise. However, because the left ventricle is compromised, the patient is not able to increase his/her heart output in response to exercise. Therefore, the heart rate is used to increase the pump speed resulting in higher mean arterial pressures.

The Level-2 algorithm (as well as Level-1 above) does not directly control the arterial pressure, i.e., LVAD outlet pressure. The arterial pressure may be indirectly controlled by the LVAD speed control because of the following two conditions: (1) the LVAD inlet and outlet pressures are not truly independent because they are coupled through the pressure difference generated across the LVAD, and (2) the Level-1 and -2 algorithms are not controlling the LVAD speed to achieve two exact pressures for the LVAD inlet and outlet, rather they are seeking an optimization solution based on a range of acceptable LVAD inlet pressures that allows some freedom in selecting a target LVAD outlet pressure. Thus the LVAD inlet pressure is the primary independent variable and its optimization within an acceptable range allows for the indirect control of the LVAD outlet pressure over a corresponding range.

The LVDFP is defined as the minimum pump inlet pressure measured over a programmable lookback period set to 3 seconds in this example. This definition ensures that the minimum pressure is captured from a period of at least one full heartbeat cycle, during some portion of which the mitral valve is open, and some portion of which the ventricle is most susceptible to suction and collapse.

An overview of the Level-1 and Level-2 control scheme is shown in FIG. 2. The Level-1 control is implemented as a standard integral speed controller with LVDFP, as represented by the measured pressure P1, as the control input and pump speed signal as its control output. The control algorithm for the Level-1 inner loop is designed to maintain the LVDFP within physician programmable limits at a desired physician programmed value when appropriate.

The Level-1 outer loop control is based on keeping the arterial pressure, as represented by the measured outlet pressure P2, within programmed limits and has a slower response time than the LVDFP inner control loop. The outer loop changes the effective desired LVDFP setpoint of the nested inner loop when the arterial pressure reaches the programmed limit values. Level-1 effectively controls the LVDFP within a programmed range whenever the arterial pressure reaches a programmed limit and controls the LVDFP to a desired value when the arterial pressure is within limits. Thus the resultant LVDFP value has been optimized because it meets the conditions of both the inner and outer loops.

The Level-2 control algorithm is implemented as an outer control loop around the inner Level-1 control loop. The control input to Level-2 is the outlet pressure, and the control output is the modified target LVDFP sent to the Level-1 control loop. When Level-2 is active and the pulse rate is above the programmed threshold, the desired target value for LVDFP is continuously modified to provide the feedback control for the target arterial pressures.

Thus the Level-2 mean arterial pressure is controlled through the intermediate mechanism of actively adjusting the Level-1 effective target value of the LVDFP within its programmed range. Note that Level-1 contains an outer feedback loop for adjusting the Level-1 LVDFP value to maintain the non-exercise mean arterial pressure within the target limits.

These non-exercise limits are suspended when Level-2 is activated and replaced by the exercise limits of the mean arterial pressure. Both the non-exercised limits and the exercise limits for the arterial pressures are physician programmable. The Level-2 outer loop control algorithm controls the LVDFP to maintain an exercise arterial pressure target value, whereas the Level-1 outer loop controls the LVDFP to maintain a non-exercise arterial pressure range.

Table 2 summarizes the priorities that the hierarchical Level-1 and Level-2 algorithms use to achieve their goals.

TABLE 2

Algorithm Hierarchy

| GOAL | LEVEL 1 CONTROL | LEVEL 2 CONTROL |
|---|---|---|
| Primary | Keep LVDFP Within Limits | Keep LVDFP Within Limits |
| Secondary | Keep Arterial Pressure Within Limits | Control to Variable Arterial Pressure Setpoint (based on BPM) |
| Tertiary | Control to LVDFP Setpoint | |

The flowrate was calculated based on the measured pressure difference across the pump and the pump performance curves. The pump performance curves were generated by measuring the flow vs. pressure difference at a series of impeller speeds of the pump. These pump curves are a characteristic of a given pump and are generally available from the pump manufacturer.

The data from these curves were entered into the LabVIEW program. During subsequent operation of the pump, the unknown value of the flow is calculated from the stored pump data through interpolation on the curves based on the measured pressure difference and the known pump impeller speed.

The power was calculated as follows. The definition of hydraulic power of a device is the product of the flowrate through the device times the pressure difference across the device. For the pump, this calculation of power is straightforward. The pressure difference is equal to the measured instantaneous pressure across the pump, P2–P1.

The flow through the pump can be measured from a flow meter during lab testing, or can be calculated in situ from pressure using the method described above.

For the left ventricle, this calculation of power is more complex. The pressure difference across the ventricular wall is calculated by subtracting the ambient barometric pressure from the internal ventricular pressure, as approximated by the pump inlet pressure, i.e. P1–P3.

The flow out of the ventricle is approximated by the flow through the pump as calculated above. This assumption is valid to the extent that all of the flow exiting the ventricle goes through the pump. When the heart recovers to the extent that the natural pumping is stronger than that of the LVAD, so that substantial flow exits through the aortic valve, this flow through the aortic valve will not be accounted for in this power calculation.

The power is accounted for only during the systolic phase, because during the diastolic phase the left ventricle is mostly passively filled, and in any event the diastolic power is negligible with respect to the systolic power. The time history of this instantaneous systolic power can be displayed as a numerical value.

The monitor in FIG. 1 shows the results of a typical test of the Level-1 control algorithm. Note that the desired inlet pressure was tested at integer values within the range of −2 to +10 mm Hg. The typical test results used a desired inlet pressure of 3.0 mm Hg and may be representative of a physician selected setpoint. Each selection of desired inlet pressure resulted in a different set of bypass flow and arterial pressure values for a given peripheral resistance.

The plotted values in FIG. 1 are representative of the state of the system at the end of the test at time T=20 seconds. The plot area shows a several second time history to T=20 seconds of the inlet pressure, the outlet pressure, and the pump control signal, which is representative of RPM. The pump control signal is scaled such that 15 mm Hg on the Y-axis corresponds to 1 V (volt) of pump control signal.

In this plot, the lower pulsating signal is the inlet pressure P1, the upper pulsating signal is the outlet pressure P2, and the smooth signal is banded between 40 and 60 mm Hg (between 2.67 and 4.00 V) and represents the pump control signal or RPM.

Before time T=3 seconds, the controller was set to manual mode with the pump signal fixed at 3V. At time T=3 seconds, the Level-1 control was enabled to bring the LVDFP to desired constant value of 3.0 mm Hg that was defined in the corresponding square indicator box.

Once enabled, the controller increased the pump signal to bring the LVDFP (seen as the valley in each inlet pressure pulse) from its uncontrolled initial value of approximately 6 mm Hg to the specified value of 3.0 mm Hg. The pump signal increased from its initial voltage of 3.00 V to a final steady state value of 3.77 V that corresponds to an initial pump speed of 3000 RPM (revolutions per minute) and a final pump speed of 3770 RPM.

The increased pump speed caused the time averaged outlet pressure to increase from its initial value of 68 mm Hg to the final value of 103.6 mm Hg. This exact value of 103.6 appearing in the corresponding circular indicator box is computed from a time averaging of the pulsing pressure over one complete heartbeat cycle. From the history plots, the characteristic response time of the system is seen as approximately 5 seconds.

Table 1 summarizes the results for 13 test runs as indicated above. FIG. 1 also shows sample setpoint values for the cooperating Level-2 control algorithms. The measured heart rate or pulse rate is 60 BPM as shown in the corresponding circular indicator box. This value is below the specified Resting Heart Rate value of 61 BPM as set in its corresponding square indicator box; so that the Level-2 control algorithm is below its threshold for controlling the exercise target values of mean arterial pressure.

In one test, the heart rate was increased to 99 BPM, representing an increase that could be caused, for example, by the patient engaging in physical exercise. The increase in heart rate above the threshold increases the Level-2 target outlet pressure linearly with heart rate. The heart rate of 99 BPM yields a target outlet pressure of 120 mm Hg. The outer control loop of Level-2 control adjusts the controller setpoint, i.e., adjusts the desired target value for LVDFP, of the inner Level-1 control loop appropriately to bring the actual outlet pressure to 119.4 mm Hg (not illustrated), near its target value of 120 mm Hg.

In this specific test, the Level-2 controller needed to increase the initial outlet pressure of approximately 100 mm Hg to the target of 120 mm Hg. An increase in outlet pressure corresponds to an increase in pump speed, which corresponds to a decrease in inlet pressure, i.e., a decrease in the desired LVDFP. To reach its target, the Level-2 controller decreased the desired LVDFP setpoint of the Level-1 controller from 2.0 to 0.0 mm Hg, which, in turn, increased the pump speed signal from 3.10 to 4.36 V, which, in turn, increased the outlet pressure from 100 to 120 mm Hg. This process took approximately 10 seconds. The mean arterial pressure of 120 mm Hg has a limit cycle variation of less than 5%.

In another test, the flowrate (in liters/min) was measured through a transonic flow meter, and was calculated from the pressure difference, pump speed, and pump characteristics. The calculated and measured flowrates agreed in mean value, but differed in the higher frequency components. The value calculated from the pressure signal had a higher frequency content and a phase that led the phase of the measured value.

Referring to FIG. 1, the power from the heart pump and heart are displayed in the lower right corner. Also displayed is the relative contribution of each to the total power output to the blood.

Table 1 shows that the mean arterial pressure, LVAD flowrates, and LVAD pump speeds increased monotonically with decreasing LVDFP setpoint. This suggests that the control algorithm should be stable through this range and that a physician should be able to select any LVDFP setpoint in this range. For this hypothetical example, the physician may use the data generated in Table 1 to program the range of acceptable values for LVDFP and arterial pressures. Note that for each patient, the physician may determine the programmed values from the unique data generated for that patient.

The results of Level-1 control shown in Table 1 also demonstrate capability for the Level-2 control algorithm. For example, if an LVDFP of 2.0 and 4.0 mm Hg are both acceptable, a secondary criterion can be applied. Selecting the lower setpoint for LVDFP (2.0 mm Hg) results in a higher value of mean arterial pressure (102 mm Hg).

The discrepancy between measured flow and pressure-calculated flow is consistent with the underlying physics behind the flow estimation technique. The pulsatile component of the pressure difference causes acceleration of the flow. The response of increased flowrate is not instantaneous, but lags the pressure because of the inertia of the pump impeller and of the columns of blood through the pump.

Thus the inertance of the system acts as a low-pass filter to the pressure signal that reduces the high frequency content transmitted to the flow signal. The solution to this is to add an appropriate inertance term to the flow calculation to filter the signal and mimic the inertance in the actual flow system. However, before filtering out (and discarding) this high frequency content, an investigation may be conducted for uncovering any diagnostic information that may exist in this high frequency signal because it is only available through pressure measurements.

The flowrate information is also useful for extrapolating the pressure signal to other locations. For example, the inlet pressure measured at the distal end of the inlet cannula 24 can be combined with the pressure drop across the inlet cannula to yield the pressure at the proximal end of the catheter, i.e., the left ventricular pressure. This correction 50 for pressure drop across the cannula is calculated by combining the flowrate information with the cannula flow resistance characteristics. The flow resistance characteristics of the pump components are calculated through analysis or measured experimentally. A similar correction 52 as described above may be effected for the outlet cannula 28 and the aorta 18.

The hydraulic power calculation values appear to be physically realistic and meaningful as demonstrated by the following example. As a reference example calculation, pumping a flow of 5 liters/min through a pressure rise of 100 mm Hg requires 1.1 watts of hydraulic power input. The pump power increases with increasing pump speed, and the ventricular power increases as the pneumatic pressure applied to the ventricle is increased. A correspondence exists between the heart power calculated by this method and the actual function of the ventricle when tested in the mock loop.

Tests of control algorithms using APS pressure sensors on standard mock loop hardware demonstrated proof-of-concept that a stable pressure-based controller could be built using such pressure sensors. The Level-1 control algorithm was able to control the pump speed in order to maintain the LVDFP within limits. The Level-2 control algorithm was able to indirectly control the specified outlet pressure to the specified target values provided that the Level-1 LVDFP was within its limits. The flowrate calculated by pressure measurements and pump characteristic curves was able to match the mean value of the measured flowrate. The hydraulic power produced by the pump and by the ventricle were calculated using the pressure measurements and provided useful information for monitoring the relative performance of the rotary assist pump versus the left ventricle.

While there have been described herein what are considered to be preferred and exemplary embodiments of the present invention, other modifications of the invention shall be apparent to those skilled in the art from the teachings herein, and it is, therefore, desired to be secured in the appended claims all such modifications as fall within the true spirit and scope of the invention.

Accordingly, what is desired to be secured by Letters Patent of the United States is the invention as defined and differentiated in the following claims in which we claim:

1. A system for assisting blood pumping through a left ventricle of a patient's heart comprising:
    a blood pump adapted to be joined in flow communication between the left ventricle and an aorta inside said patient;
    an inlet pressure sensor for measuring inlet pressure of blood flow to said pump from said left ventricle;
    a controller operatively joined to said inlet pressure sensor, and to said pump for controlling operation thereof, and including:
        means including a summing junction for comparing said measured inlet pressure with a set value of said inlet pressure to determine a difference therebetween; and
        means for adjusting speed of said pump in a closed loop control using feedback of said measured inlet pressure at said summing junction to minimize said pressure difference between said measured inlet pressure and said set value thereof.

2. A system according to claim 1 wherein said controller further comprises means for limiting said measured inlet pressure to a preselected first range having a minimum value for preventing collapse of said left ventricle.

3. A system according to claim 2 further comprising:
    an outlet pressure sensor operatively joined to said controller for measuring outlet pressure of said blood flow from said pump to said aorta; and said controller further includes an outer closed loop control for adjusting speed of said pump using feedback of said measured outlet pressure for maintaining said outlet pressure in a preselected second range, with feedback of said measured inlet pressure being used in a cooperating inner closed loop control for maintaining said inlet pressure in said first range.

4. A system according to claim 3 wherein said outer loop control is further configured to adjust said inlet pressure within said first range for maintaining said outlet pressure within said second range.

5. A system according to claim 4 wherein said controller is further configured for measuring said inlet pressure over a period of at least one full heartbeat cycle, and said inlet pressure consists of the minimum value thereof during said period.

6. A system according to claim 5 further comprising:
a reference pressure sensor disposed adjacent to skin of said patient for measuring atmospheric pressure thereat; and
said controller is further configured for correcting said measured inlet and outlet pressures to gauge pressure using said reference pressure.

7. A system according to claim 6 further comprising:
means for measuring heart rate of the patient's heart; and
said controller further includes a second level of control for increasing speed of said pump to increase said outlet pressure for measured heart rates greater than a specified resting heart rate.

8. A system according to claim 7 wherein said controller is further configured for suspending said second range of outlet pressure when said second level control increases said pump speed; and
replacing said second range with a different preselected third range of said outlet pressure.

9. A system according to claim 8 wherein said second control level in said controller is configured for increasing said outlet pressure from said pump by adjusting said inlet pressure.

10. A system according to claim 9 wherein:
said second range includes preselected maximum and minimum values of said outlet pressure;
said third range includes a different preselected maximum value of said outlet pressure, a preselected maximum percent increase of said outlet pressure above said outlet pressure at said resting heart rate, and a preselected maximum increase in said heart rate; and
said outlet pressure is increased in response to increase in said heart rate as derived from said third range.

11. A system according to claim 9 wherein said heart rate measuring means are effective for measuring periodic pulses in said inlet pressure corresponding with beating of said heart.

12. A system according to claim 9 further comprising:
means for measuring speed of said pump; and
said controller is further configured for determining pressure differential between said measured outlet and inlet pressures;
said controller is further configured for determining flowrate through said pump using predetermined performance curves for said pump based on said measured speed and pressure differential; and
said controller is further configured for determining pumping power for said pump as the product of said pressure differential and flowrate determined therefrom.

13. A system according to claim 12 wherein said controller includes a third level of control of said inlet pressure for adjusting speed of said pump to control pumping power of said pump.

14. A system according to claim 13 wherein said controller is further configured for:
determining pumping power for said left ventricle; and
adjusting said pumping power of said pump to correspondingly share pumping load between said pump and said left ventricle.

15. A method of controlling a blood pump joined in flow communication between a left ventricle and aorta of a patient's heart comprising:
measuring inlet pressure of blood flow to said pump from said left ventricle;
comparing said measured inlet pressure with a set value of said inlet pressure to determine a difference therebetween; and
adjusting speed of said pump in a closed control loop using feedback of said measured inlet pressure to minimize said pressure difference between said measured inlet pressure and said set value thereof.

16. A method according to claim 15 further comprising limiting said measured inlet pressure to a preselected first range having a minimum value for preventing collapse of said left ventricle.

17. A method according to claim 16 wherein said first range includes a maximum value of said inlet pressure for preventing overburdening of the patent's right heart.

18. A method according to claim 17 further comprising:
measuring outlet pressure of said blood flow from said pump to said aorta; and
adjusting speed of said pump in an outer closed loop control using feedback of said measured outlet pressure for maintaining said outlet pressure in a preselected second range, with said feedback of said measured inlet pressure being used in a cooperating inner closed loop control for maintaining said inlet pressure in said first range.

19. A method according to claim 18 wherein said outer loop control adjusts said inlet pressure within said first range for maintaining said outlet pressure within said second range.

20. A method according to claim 19 wherein said inlet pressure is measured over a period of at least one full heartbeat cycle, and consists of the minimum value during said period.

21. A method according to claim 20 wherein said outer loop control has a slower response time than said inner loop control.

22. A method according to claim 20 further comprising correcting said measured inlet pressure to conform with pressure inside left ventricle.

23. A method according to claim 20 further comprising correcting said measured outlet pressure to conform with pressure inside said aorta.

24. A method according to claim 20 further comprising:
joining said pump in parallel flow between said left ventricle and said aorta external of said heart;
measuring atmospheric reference pressure at skin of the patient; and
correcting said measured inlet and outlet pressures to gauge pressure using said reference pressure.

25. A method according to claim 20 further comprising:
specifying a resting heart rate for the patient;

measuring heart rate of the patient's heart; and increasing speed of said pump in a second level of control to increase said outlet pressure for measured heart rate greater than said resting heart rate.

26. A method according to claim 25 further comprising:

suspending said second range of outlet pressure when said second level control increases said pump speed; and replacing said second range with a different preselected third range of said outlet pressure.

27. A method according to claim 26 wherein said second level control increases said outlet pressure from said pump by adjusting said inlet pressure.

28. A method according to claim 26 wherein:

said second range includes preselected maximum and minimum values of said outlet pressure;

said third range includes a different preselected maximum value of said outlet pressure, a preselected maximum percent increase of said outlet pressure above said outlet pressure at said resting heart rate, and a preselected maximum increase in said heart rate; and said outlet pressure is increased in response to increase in said heart rate as derived from said third range.

29. A method according to claim 26 wherein said heart rate is measured by measuring periodic pulses in said inlet pressure corresponding with beating of said heart.

30. A method according to claim 26 further comprising:

measuring speed of said pump;

determining pressure differential between said measured outlet and inlet pressures;

determining flowrate through said pump using predetermined performance curves for said pump based on said measured speed and pressure differentials; and determining pumping power for said pump as the product of said pressure differential and said flowrate determined therefrom.

31. A method according to claim 30 further comprising adjusting said speed of said pump in a third level of control of said inlet pressure to control pumping power of said pump.

32. A method according to claim 31 further comprising:

determining pumping power for said left ventricle; and adjusting pumping power of said pump to correspondingly share pumping load between said pump and said left ventricle.

33. A method according to claim 26 further comprising monitoring said inlet and outlet pressures, and performance of said pump to diagnose abnormalities therewith.

* * * * *